United States Patent [19]

Moriuchi et al.

[11] Patent Number: 4,733,566
[45] Date of Patent: Mar. 29, 1988

[54] PRESSURE TRANSDUCER APPARATUS

[75] Inventors: Yousuke Moriuchi; Tadashi Kohsai, both of Fujinomiya, Japan

[73] Assignee: Terumo Kabushiki Kaisha, Tokyo, Japan

[21] Appl. No.: 900,732

[22] Filed: Aug. 27, 1986

[30] Foreign Application Priority Data

Aug. 30, 1985 [JP] Japan .................... 60-132646[U]

[51] Int. Cl.$^4$ .................... G01L 7/08; G01L 9/00
[52] U.S. Cl. .................... 73/756; 73/723; 128/748
[58] Field of Search .................... 73/756, 723–728; 137/625.16, 625.47; 128/748, 667, 672, 673, 674, 675

[56] References Cited

U.S. PATENT DOCUMENTS

| | | | |
|---|---|---|---|
| 1,148,217 | 7/1915 | Charles | 137/625.16 |
| 1,383,100 | 6/1921 | Green | 137/625.16 |
| 2,702,050 | 2/1955 | Thomas | 137/625.16 |
| 3,057,350 | 10/1962 | Cowley | 137/625.41 |
| 3,610,228 | 10/1971 | Temkin | 128/748 |

Primary Examiner—Donald O. Woodiel
Attorney, Agent, or Firm—Frishauf, Holtz, Goodman & Woodward

[57] ABSTRACT

A fluid pressure transducer apparatus comprising a fluid pressure transducer mechanism and a fluid pressure-transmitting path. The fluid pressure transducer mechanism includes a fluid pressure detection mechanism, having a detection surface of a fluid pressure, for converting a fluid pressure into an electrical signal, and a chamber, formed on the detection surface, for storing a fluid. The path includes a cylindrical member having a first port communicating with the chamber and a plurality of second ports arranged on a surface perpendicular to an axis of the cylindrical member, and a stop cock arranged in the cylindrical member to be slidable with an inner surface of the cylindrical member. The stop cock has a path defined therein and a handle for slidably rotating the stop cock in the cylindrical member through a predetermined angle so that the path communicates the first port with only one of the plurality of second ports and no other second ports communicate with each other.

2 Claims, 10 Drawing Figures

4,733,566

PRESSURE TRANSDUCER APPARATUS

BACKGROUND OF THE INVENTION

1. Field of the Invention

The present invention relates to a pressure transducer apparatus and, more particularly, to a pressure transducer apparatus having a stop cock and suitable for use in an invasive fluid pressure monitoring system, e.g., an invasive blood pressure monitering system.

2. Description of the Prior Art

A pressure transducer is conventionally used in order to measure a dynamic blood pressure. Since a pressure transducer has a high precision and is capable of continuous measurement and measurement of low pressures, a dynamic blood pressure can be graphically measured. In particular, the pressure transducer is inevitable for monitoring a patient in serious condition. The pressure transducer detects the dynamic blood pressure by converting it into an electrical signal.

When dynamic pressures in a plurality of blood vessel systems (e.g., artery and vein) are sequentially measured by a single pressure transducer, blood in each blood vessel system to be measured must reach a detection section of the pressure transducer and other blood vessel systems must not communicate with each other. For this purpose, conventionally, catheter lines communicating with the respective blood vessel system are connected through two to five three-port stop cocks, and paths of the three-port stop cocks are appropriately switched to attain the above requirements.

However, use of such a three-port stop cock results in a complex switching operation. If the stop cocks are erroneously operated, different blood vessel systems communicate with each other, and a serious accident that may threaten the life of a patient (for example, artery blood flows into venous blood) may be caused.

SUMMARY OF THE INVENTION

It is therefore an object of the present invention to provide a pressure transducer apparatus having a stop cock which is easy to operate and will not therefore invite an erroneous operation by the operator.

According to the present invention, there is provided a fluid pressure transducer apparatus comprising:

(A) a fluid pressure transducer mechanism including, (A-i) a fluid pressure detection mechanism, having a detection surface of a fluid pressure, for converting a fluid pressure into an electrical signal, and (A-ii) a chamber, formed on the detection surface, for storing or receiving a fluid; and (B) path means, selectively communicating the chamber with a fluid pressure measurement portion, for transmitting a fluid pressure of the measurement portion to the detection surface, including:

(B-i) a cylindrical member having a first port communicating with the chamber and a plurality of second ports arranged on a surface perpendicular to an axis of the cylindrical member, and (B-ii) a stop cock arranged in the cylindrical member to be slidable with an inner surface of the cylindrical member, the stop cock having a path defined therein and handle means for slidably rotating the stop cock in the cylindrical member through a predetermined angle so that the path communicates the first port with only one of the plurality of second ports and no other second ports communicate with each other.

Claims of the present invention include a stop cock mechanism constituting the path means.

DETAILED DESCRIPTION OF THE PREFERRED EMBODIMENT

The present invention will be described in detail with reference to the accompanying drawings.

Figure 1:
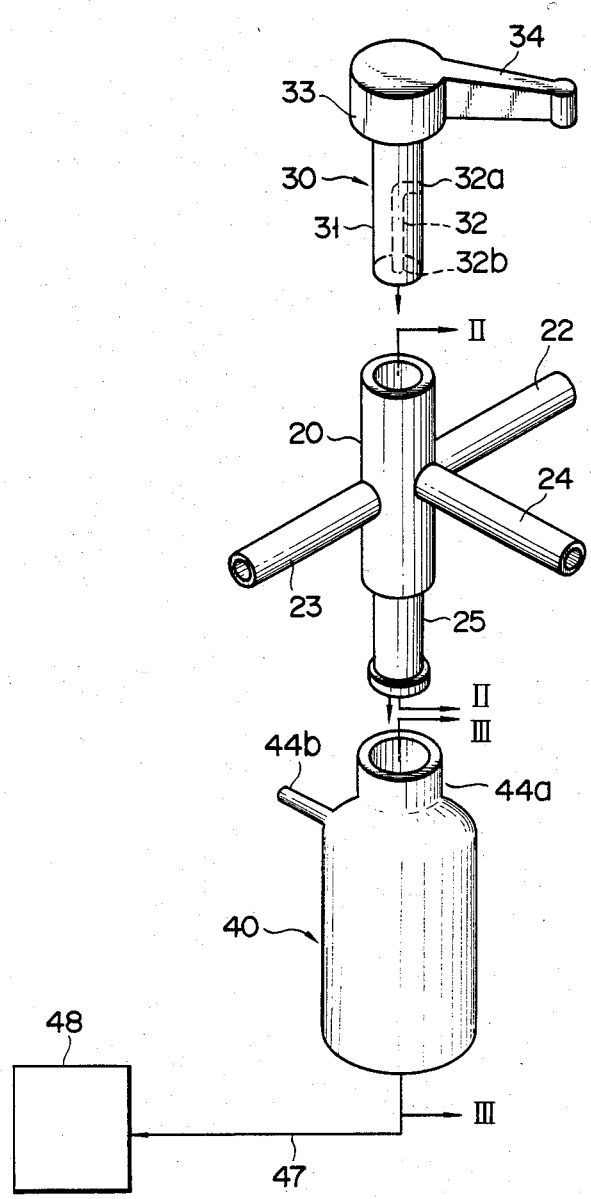
FIG. 1 is a perspective view schematically showing a pressure transducer apparatus of the present invention.

FIG. 1 shows a pressure transducer apparatus having a stop cock according to the present invention. The apparatus has stop cock 30 with cylindrical member 20 and handle 34, and pressure transducer 40.

Figure 2:
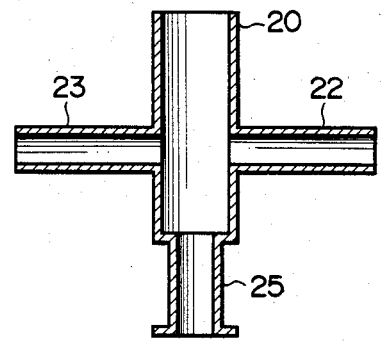
FIG. 2 is a sectional view of a cylindrical member shown in FIG. 1.

As can be seen from the sectional view of FIG. 2, three second hollow cylindrical ports 22, 23, and 24 communicating with cylindrical member 20 are arranged integrally on a surface perpendicular to the axial direction of cylindrical member 20. The second ports are located on an identical plane, and extend in directions orthogonal to each other. The outer surfaces of the second ports are preferably tapered so as to allow easy communication with other members.

First hollow cylindrical port 25 coaxially extends from the bottom surface of cylindrical member 20. Port 25 communicates with the interior of member 20, and is formed intergrally therewith. The outer surface of port 25 is preferably tapered to allow easy connection with the pressure transducer.

Cylindrical member 20, second ports 22, 23, and 24, and first port 25 are integrally formed of a thermoplastic resin having a relatively high hardness, e.g., polycarbonate or nylon.

Stop cock 30 having handle 34 includes columnar body 31. Columnar body 31 has an outer diameter equal to or slightly larger than the inner diameter of cylindrical member 20. When stop cock 30 having handle 34 is tightly fitted in cylindrical member 20, it is slidable and rotatable therein. In this case, in order to reduce a slide resistance, silicone oil or reactive silicone can be coated on the outer peripheral surface of columnar body 31 of stop cock 30 having handle 34.

Through path 32 is formed in columnar body 31 to extend from its outer peripheral surface to bottom surface. Path 32 is open to the outer peripheral surface and the bottom surface of columnar body 31 (openings 32a and 32b, respectively). Opening 32b communicates with port 25 formed on member 20. Opening 32a is formed at a position in the outer peripheral surface of body 31 at which it coincides with an opening of second port 22, 23, or 24 when body 31 is inserted in cylindrical member 20.

Head 33 having a diameter larger than that of body 31 is formed on the upper portion of columnar body 31, and handle 34 for rotating body 31 inside member 20 is formed integrally with head 33.

Stop cock 30 having handle 34 is formed of a thermoplastic resin having a relatively low hardness, e.g., polyethylene or polypropylene.

Figure 3:
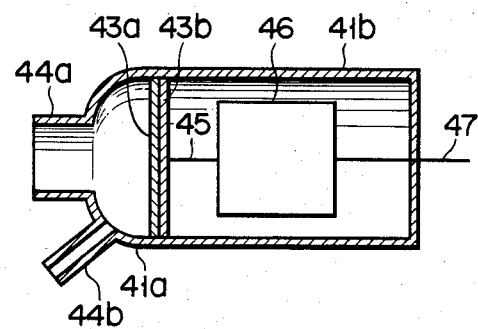
FIG. 3 is a schematical sectional view of a pressure transducer.

Pressure transducer 40 is well known to those skilled in the art, and is described in, for example, "SHIN-IRYO", Vol. 11, No. 3 (1984), pp. 25 to 27. The structure of pressure transducer 40 will be described also with reference to FIG. 3. Pressure transducer 40 comprises casing 41b having pressure-receiving metal film 43b and casing 41a screwed in the head portion of casing 41b. In addition, pressure transducer 40 has pressure-receiving plastic film 43a which is in tight contact with film 43b and is liquid-tightly fixed to casing 41a when casings 41a and 41b are screwed together. Casing 41a has two fluid columns 44a and 44b in a dome-shaped chamber storing a fluid.

The internal structure of casing 41b will be described below. Pressure-receiving metal film 43b is connected to transducer element 46 for converting a fluid pressure into an electrical signal through insulator 45, and the electrical signal is derived through cable 47. Cable 47 is connected to, e.g., television monitor 48 (FIG. 10), and the fluid pressure is displayed thereon.

Figure 4:
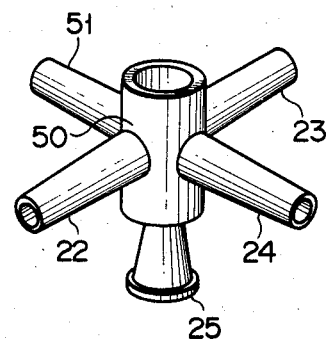
FIGS. 4 to 9 are perspective views and sectional views showing a stop cock used in the present invention.

FIG. 4 shows another cylindrical member 50 used instead of cylindrical member 20 of the pressure transducer of the present invention described with reference to FIG. 1. The difference between cylindrical members 50 and 20 (FIG. 1) is that another second port is added to member 50. Additional port 51 is located in an identical plane as other second ports 22, 23, and 24.

Figure 5:
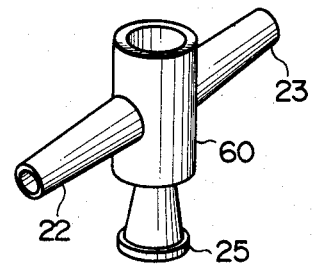

FIG. 5 shows still another cylindrical member 60 used instead of cylindrical member 20 of the pressure transducer of the present invention shown in FIG. 1. The difference between members 60 and 20 (FIG. 1) is that member 60 has only two second ports.

Figure 6:
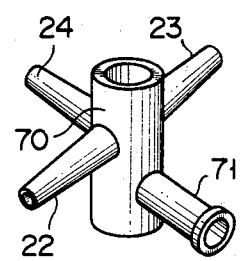
Figure 7:
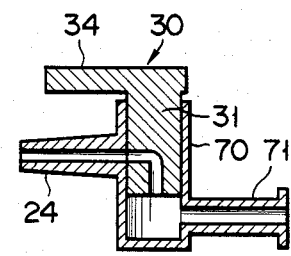

FIG. 6 shows still another cylindrical member 70 used instead of cylindrical member 20 shown in FIG. 1. The difference between cylindrical members 70 and 20 (FIG. 1) is that first port 71 is arranged on the outer peripheral surface of cylindrical member 70 toward its bottom side. In this case, columnar body 31 of a stop cock having a handle is arranged as shown in the sectional view in FIG. 7, so that the bottom surface of body 31 does not close port 71.

Figure 8:
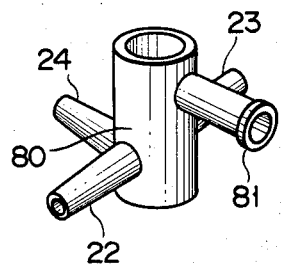
Figure 9:
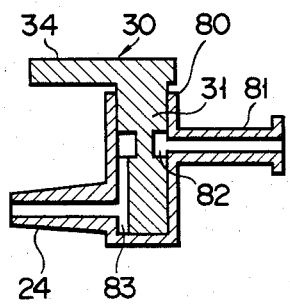

Cylindrical member 80 shown in FIG. 8 has first port 81 on its upper portion. In this case, annular groove 82 is formed in the outer peripheral surface of stop cock 30 having handle 34. Annular groove 82 is formed at a position corresponding to that of port 81, as shown in the sectional view of FIG. 9. Vertical groove 83 is formed in columnar body 31 to extend from groove 82 to the bottom portion of body 31, and forms a fluid path communicating with port 81 regardless of the position of handle 34.

Figure 10:
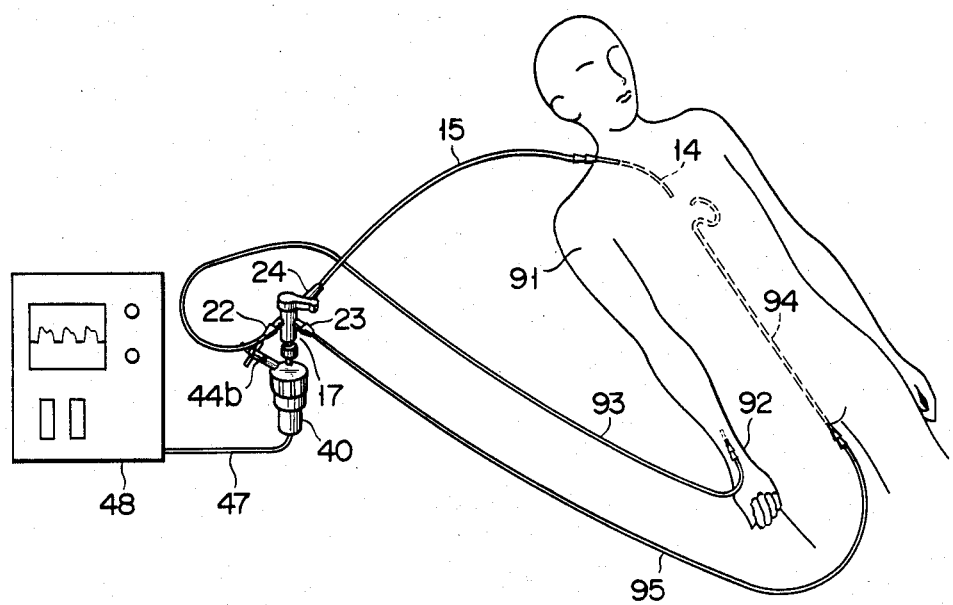
FIG. 10 is a representation for explaining the operation of the pressure transducer of the present invention.

The operation of the pressure transducer apparatus of the present invention described above will be described with reference to the apparatus shown in FIGS. 1 and 10. As shown in FIG. 10, peripheral-artery indwelling catheter 92 is indwelled in the artery of patient 91, and is connected to second port 22 through tube 93. Lung-artery indwelling catheter 94 is indwelled in the lung artery, and is connected to second port 23 through tube 95. Central-vein indwelling catheter 14 is indwelled in the central vein and is connected to second port 24 through tube 15.

In order to measure blood pressures in the respective blood vessels, opening 32a of columnar body 31 of stop cock 30 having handle 34 is turned to coincide with second port 22, 23, or 24. A pressure transmitted from the peripheral artery, central vein, or lung artery through the corresponding catheter and tube is converted into an electrical signal by pressure transducer 40, and is displayed on television monitor 48.

Stop cock 30 having handle 34 in the apparatus of the present invention communicates with second port 22, 23, or 24 only through opening 32a, and the other opening 32b communicates with only first port 25 connected to pressure transducer 40. Therefore, second ports 22, 23, and 24 will not communicate with each other regardless of the position of handle 34. In addition, a catheter communicating with transducer 40 can be easily identified simply by checking the position of handle 34.

According to the present invention as described above, pressures in a plurality of blood vessels can be easily and sequentially measured without causing an erroneous operation.

What is claimed is:

1. A fluid pressure transducer apparatus comprising:
   (A) a fluid pressure transducer means including:
   (A-i) a fluid pressure detection means, having a detection surface of a fluid pressure, for converting a fluid pressure into an electrical signal, and
   (A-ii) a chamber, formed on said detection surface, for storing a fluid; and
   (B) a path means, selectively communicating said chamber with a fluid pressure measurement portion, for transmitting a fluid pressure of the measurement portion to said detection surface, said path means including:
   (B-i) a cylindical member having a first port communicating with said chamber and a plurality of second ports arranged on a surface substantially perpendicular to an axis of said cylindrical member, said first port being arranged on an upper portion of said cylindrical member, and
   (B-ii) a stop cock arranged in said cylindrical member to be slidable with respect to an inner surface of said cylindrical member, said stop cock having a path defined therein and handle means for slidably rotating said stop cock in said cylindrical member through a predetermined angle so that said path communicates said first port with only one of said plurality of second ports and no other second ports communicate with each other, said stop cock further having an annular groove communicating with said first port and a substantially vertical groove communicating said annular groove and said second ports one at a time.

2. A stop cock device for selectively switching fluid paths, comprising:
   a cylindrical member having a first port and a plurality of second ports arranged in a plane substantially perpendicular to an axis of said cylindrical member, said first port being arranged on an upper portion of said cylindrical member, and
   a stop cock arranged in said cylindrical member to be slidable with respect to an inner surface of said cylindrical member, said stop cock having a path defined therein and handle means for slidably rotating said stop cock in said cylindrical member through a predetermined angle so that said path communicates said first port with only one of said plurality of second ports and no other second ports communicate with each other, said stop cock having an annuar groove communicating with said first port and a substantially vertical groove communicating said annular groove and said second ports one at a time.

* * * * *